United States Patent [19]

Hosaka

[11] 3,943,660

[45] Mar. 16, 1976

[54] POLLINATOR

[75] Inventor: Hideo Hosaka, Takasaki, Japan

[73] Assignee: Max Kabushiki Kaisha, Tokyo, Japan

[22] Filed: June 3, 1974

[21] Appl. No.: 475,750

[30] Foreign Application Priority Data

June 9, 1973 Japan .......................... 48-68042[U]
Nov. 19, 1973 Japan .......................... 48-133553[U]

[52] U.S. Cl. .................................... 47/1.41; 222/193
[51] Int. Cl.² ...................... A01G 7/00; A01H 1/02
[58] Field of Search ............. 47/1.41; 222/383, 385, 222/193, 541; 169/32; 239/362, 363, 355, 547

[56] References Cited

UNITED STATES PATENTS

| | | | |
|---|---|---|---|
| 2,548,487 | 4/1951 | Marchant et al. | 47/1.41 |
| 2,802,302 | 8/1957 | Yost | 47/1.41 |
| 3,291,350 | 12/1966 | Malec | 222/383 X |
| 3,462,082 | 8/1969 | Everett | 222/193 X |
| 3,674,209 | 7/1972 | Liedberg | 222/193 X |

*Primary Examiner*—Stephen C. Pellegrino
*Attorney, Agent, or Firm*—Woodhams, Blanchard and Flynn

[57] ABSTRACT

A hand-held pollinator comprising a casing having a pump mechanism mounted therein. A pollen storage container is removably attached to the casing and a discharge conduit from the pump extends into the pollen storage chamber for pressurizing same. A powder discharge conduit has the inner end thereof in communication with the chamber and has a nozzle on the outer end thereof for permitting pollen entrained in an airstream to be discharged therethrough when the pump mechanism is energized. An enlarged conical cover can be mounted to surround the discharge nozzle if desired. The housing has a power source, such as a battery, mounted thereon and has a movable trigger which, when manually depressed, electrically connects the power source to a motor associated with the pump mechanism.

10 Claims, 5 Drawing Figures

II
1
2
2A
2B
26
27
28

3
26
B
16
2
15
6
10
27
9
A
11
14
4
5
C
17
13
18
12
1
24
D
23
25
8
7
33
32
29
31
30

18
26
20
22
19
21
24
23
25
8

POLLINATOR

FIELD OF THE INVENTION

The present invention relates to an implement to be employed for mechanically conducting a pollinating operation.

BACKGROUND OF THE INVENTION

In conventional practice, an agricultural operation for pollination is conducted by the employment of a hair pencil, a cotton bar, or the like. This pollination operation requires many hours of labor, is fatiguing to the laborer, and requires a substantial number of laborers. This operation also does not permit application of a measured quantity of pollen, and the quantity of pollen as applied is subject to dispersion and waste, and hence unsuccessful pollination is effectuated in many cases.

The present invention relates to such a new and novel pollinator which is capable of eliminating the abovementioned disadvantages.

DETAILED DESCRIPTION

Figure 1:
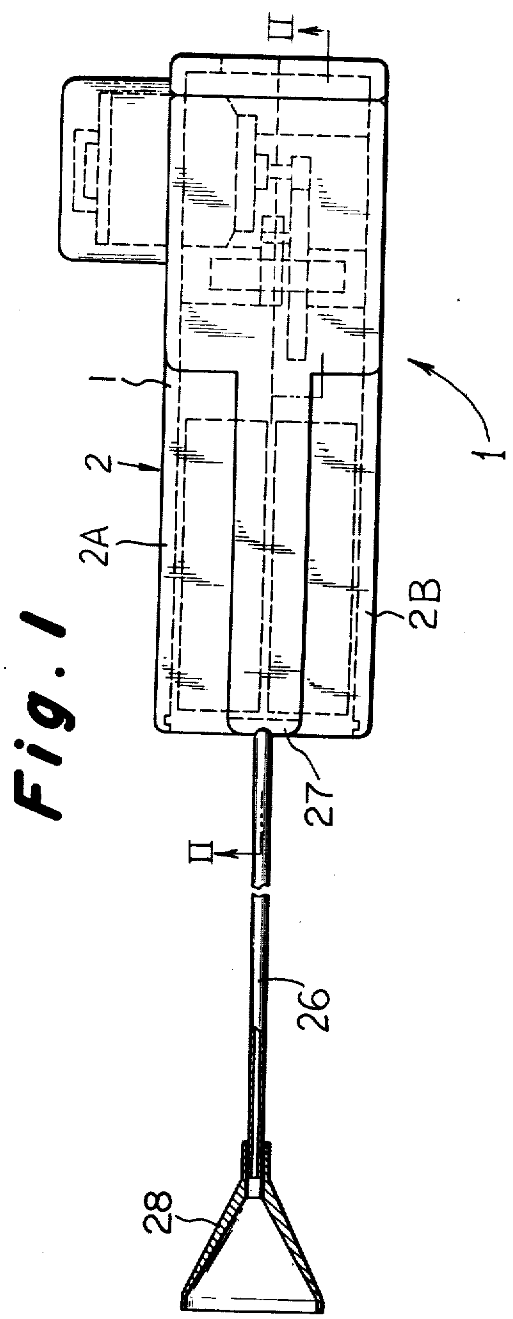
FIG. 1 is a plan view of a pollinator according to the present invention.
Figure 2:
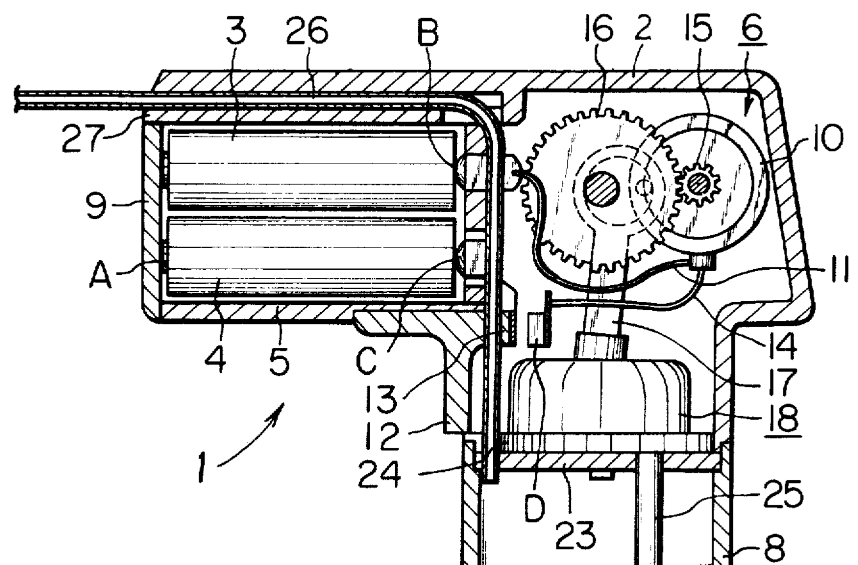
FIG. 2 is a sectional view as taken along the line II—II in FIG. 1.
Figure 3:
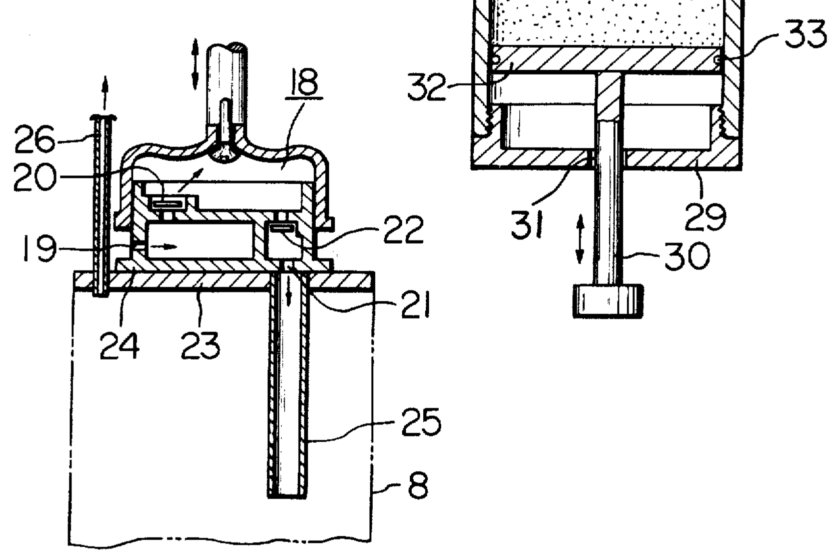
FIG. 3 is a longitudinal sectional view of the pollen injection pump shown in FIG. 2.

FIGS. 1 and 2 illustrate a pollinator 1 according to the present invention. Pollinator 1 has a pistol-shaped housing or casing 2 which is divided into opposed sections 2A and 2B which are fixed together. The front end of casing 2 has a section 5 for containing dry batteries 3 and 4, and the rear end of casing 2 has a pump driving mechanism 6 mounted therein. Casing 2 also has a storage container 8 for pollen 7, which container 8 is removably attached to the rear lower end of the casing. The section 5 has a cap 9 provided with a terminal A properly set in place at the open end thereof in such a manner as to be removable at liberty. Section 5 also has terminals B and C mounted thereon adjacent the inner end of the battery compartment. Terminal B is connected with a cord 11 which connects with a motor 10, and terminal C functioning concurrently as a return spring for a movable trigger member 12 arranged at the rear end of section 5. One end of terminal C is connected with the rear end 13 of the trigger 12 and is constructed in such a manner as to be caused to come into contact with a terminal D connected with another cord 14 which connects with the motor 10.

The pump driving mechanism 6 as positioned in the rear of the casing 2 includes the motor 10, a pinion 15 nonrotatably mounted on the motor shaft, a crown gear 16 driven by gear 15, a connecting rod 17 pivoted eccentrically with the crown gear 16, and a pump 18 activated by the reciprocating motion of the connecting rod 17. The pump 18 comprises a sealed surrounding wall made of a rubbery flexible material having the top end thereof jointed with the connecting rod 17. Pump 18 is supplied with fluid by a suction valve 20 in communication with an intake vent 19, which vent 19 is formed in an intermediate member 24 which is fixedly positioned on a base plate 23, the plate 23 being fixed on the casing 2.

The upper open end of a vinyl pipe 25 is connected with an exhaust vent 21, which pipe 25 extends into the interior of the pollen storage container 8. An injection pipe 26 for the pollen 7 has the lower end thereof mounted on the pump base 23, and the upper or discharge end of the injection pipe 26 projects forwardly from the top end 27 of the casing 2. A conical or trumpet-shaped cover 28 is mounted on the discharge end of pipe 26 in such a manner as to be removable when desired.

The pollen storage container 8 has a removable cap 29 properly set in place on the lower end thereof. The cap 29 has a hole 31 therethrough for an adjusting rod or slide 30, and a movable plate or piston 32 is positioned on the adjusting rod and is slidably supported on the internal wall of the pollen storage container 8. The sliding surface of the movable plate 32 has an elastomeric O-ring 33 properly fitted thereon.

OPERATION

To operate the pollinator 1, the trigger 12 is activated by pushing same rearwardly by a finger. This causes terminals C and D to contact each other, whereby the circuit arranged between the motor 10 and the batteries 3, 4 is closed so as to rotate the motor 10. The energization of the motor 10 causes the pinion 15 and the crown gear 16 to rotate, and accordingly, a cranking motion is imposed on the connecting rod 17 which causes expansion and contraction of the sealed surrounding wall made of flexible material of the pump 18. Thus, air is suctioned from the outside atmosphere through the intake vent 19 and the valve 20 into the pump chamber. The air in the pump chamber is then blown into the pollen storage container 8 through the exhaust valve 22, the exhaust vent 21, and the pipe 25. The pollen 7 in the storage container 8, together with the air, is then forced through the pipe 26, whereby the pollen is ejected through the nozzle 28.

Thus, the pollinator 1 permits a pollinating operation to be conducted readily and quickly while using only a single hand. The present invention also permits a substantially constant quantity of atomized pollen to be ejected at all times, thus enabling pollination to be conducted in an economical and effective manner, while also avoiding wasting of pollen.

Further, replacement of a consumed dry battery with a new one and supplement of pollen can be conducted by a simple operation through the removal of the caps.

Furthermore, when the pollen in the storage container is reduced in quantity in a gradual manner in the course of the consumption thereof, the volume of the air in the pollen storage container is correspondingly increased, which can thus result in a reduction in the quantity of the pollen being ejected. However, with such a situation taken into due consideration, and for the purpose of eliminating such a foreseeable defect, the movable bottom plate 32 so fitted in the pollen storage container 8 as to be capable of sliding therein is properly designed so as to be movable at liberty by the adjusting rod 30 for controlling the volume of the pollen storage container, thereby keeping the proportion of pollen to air in the said container at a fairly constant ratio. Thus, a constant quantity of pollen can be ejected at all times.

Figure 4:
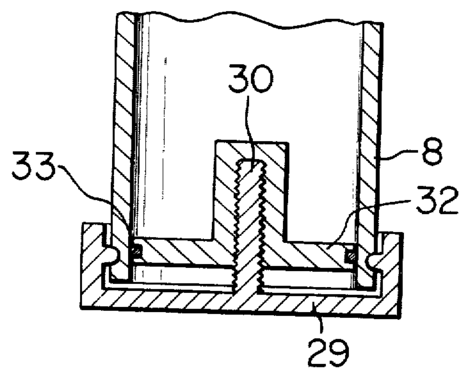
FIGS. 4 and 5 are sectional views of a modification of a quantitative pollen injection control device.
Figure 5:
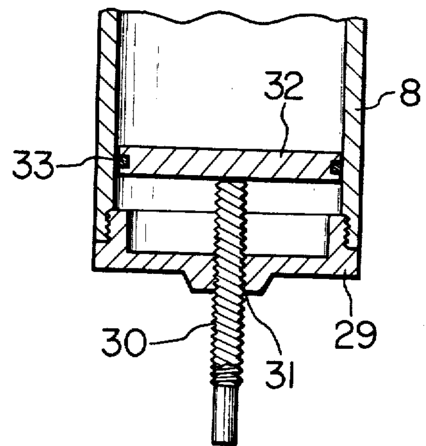

FIG. 4 and FIG. 5 are illustrations of other means for effectuating control over the movable bottom plate 32.

In FIG. 4, a threaded control rod 30 extends upwardly on the cap 29, and the rod 30 is threadably engaged with the bottom plate 32. Cap 29 is rotatably supported on the lower end of container 8, whereby the movable bottom plate is caused to move in a sliding manner into the pollen storage container.

In the case of the illustration shown in FIG. 5, the through-hole 31 drilled through the cap 29 is threaded and is engaged with the threaded adjusting rod 30. The adjusting rod 30 can be rotated at liberty, whereby the movable bottom plate 32 is caused to move in a sliding manner into the pollen storage container.

The trumpet-shaped cover 28 mounted on the discharge end of the ejection pipe 26, which cover 28 can be removed if desired, prevents the discharge nozzle of the pipe 26 from coming into direct contact with petals and leaves moistened and wet with dew, rainfall, or the like. This prevents the discharge nozzle from becoming clogged by moistened and wet pollen. Cover 28 also keeps discharged pollen from being blown away, even in a high wind, until a satisfactory pollinating operation can be ensured.

What is claimed is:

1. A pollination device, comprising:

housing means defining a substantially pistol-shaped casing having a substantially horizontal and elongated upper section, said casing also having a hollow lower section projecting downwardly from the upper section adjacent one end thereof;

a pollen storage container attached to said housing means and defining therein a compartment adapted to contain a quantity of pollen, said pollen storage container being removably mounted on the lower end of said lower section;

a power source mounted on said housing means, said power source including battery means removably positioned within said upper section adjacent the other end thereof;

pump means mounted on said housing means for supplying air into said compartment, said pump means being positioned within said casing adjacent said one end of said upper section and having a discharge port connected so as to communicate with said compartment;

conduit means providing communication between said compartment and a location disposed externally thereof for permitting discharge of pollen from said compartment, said conduit means having the inlet end thereof positioned in communication with said compartment and having a discharge nozzle formed on the outlet end thereof; and actuator means for actuating said pump means to cause air to be supplied to said compartment so that the air picks up the pollen in said compartment and discharges same through said discharge nozzle, said actuator means including manually-actuated electrical switch means mounted on said housing means for connecting said power source to said pump means for activating same, said electrical switch means including at least one manually actuated switch portion movably mounted on said housing means and positioned for manual actuation.

2. A device according to claim 1, wherein said device is small and capable of being held in one hand.

3. A device according to claim 1, wherein said pump means includes a motor electrically interconnected to said battery means, a reciprocating pump member, and reciprocating linkage means drivingly connected between said motor and said pump member for converting the rotation of said motor into reciprocation of said pump member.

4. A pollination device, comprising:

housing means;

a pollen storage container attached to said housing means and defining therein a compartment adapted to contain a quantity of pollen;

pump means mounted on said housing means for supplying air into said compartment, said pump means having a discharge port;

a discharge pipe connected to the discharge port of said pump means and extending into the interior of said compartment so that the outlet end of said discharge pipe is immersed within the quantity of pollen contained within said compartment;

conduit means fixed relative to said housing means and providing communication between said compartment and a location disposed externally thereof for permitting discharge of pollen from said compartment, said conduit means having the inlet end thereof positioned in communication with said compartment and having a discharge nozzle formed on the outlet end thereof; and actuator means for actuating said pump means to cause air to be supplied to said compartment so that the air picks up the pollen in said compartment and discharges same through said discharge nozzle.

5. A pollination device, comprising:

housing means;

a pollen storage container attached to said housing means and defining therein a compartment adapted to contain a quantity of pollen;

pump means mounted on said housing means for supplying air into said compartment, said pump means having a discharge port connected so as to communicate with said compartment;

said pump means comprising a pump member constructed of a flexible material and defining a pump chamber, said pump means also including a driving member drivingly connected to said flexible member for causing reciprocation of same to repetitively vary the volume of said pump chamber;

conduit means fixed relative to said housing means and providing communication between said compartment and a location disposed externally thereof for permitting discharge of pollen from said compartment, said conduit means having the inlet end thereof positioned in communication with said compartment and having a discharge nozzle formed on the outlet end thereof; and actuator means for actuating said pump means to cause air to be supplied to said compartment so that the air picks up the pollen in said compartment and discharges same through said discharge nozzle.

6. A pollination device, comprising:

housing means;

a pollen storage container attached to said housing means and defining therein a compartment adapted to contain a quantity of pollen;

adjustment means associated with said pollen storage container for varying the volume of said compartment for controlling the volume ratio of pollen to air;

pump means mounted on said housing means for supplying air into said compartment, said pump means having a discharge port connected so as to communicate with said compartment;

conduit means fixed relative to said housing means and providing communication between said compartment and a location disposed externally thereof for permitting discharge of pollen from said compartment, said conduit means having the inlet end thereof positioned in communication with said compartment and having a discharge nozzle formed on the outlet end thereof; and actuator means for actuating said pump means to cause air to be supplied to said compartment so that the air picks up the pollen in said compartment and discharges same through said discharge nozzle.

7. A device according to claim 6, wherein the adjustment means includes a pistonlike bottom plate slidably positioned within said compartment and selectively movable along said compartment for varying the volume thereof.

8. A portable hand-held power dispensing device, comprising:

portable housing means defining therein a substantially closed chamber, said housing means including a horizontally elongated tubular housing portion defining said chamber therein;

a powder storage container fixedly attached to said housing means and defining therein a compartment adapted to contain a quantity of powder, said storage container being attached to and projecting downwardly from said housing means adjacent one end of said elongated tubular housing portion, said housing means and said storage container defining a pistol-shaped configuration;

pump means mounted on said housing means and positioned within said chamber for supplying air into said compartment, said pump means having a discharge port connected so as to communicate with said compartment;

electrical motor means drivingly connected to said pump means, said motor means being mounted on said housing means and disposed within said chamber;

battery means disposed within said chamber for energizing said motor means;

conduit means providing communication between said compartment and a location disposed externally thereof for permitting discharge of powder from said compartment, said conduit means having the inlet end thereof positioned in communication with said compartment and having a discharge nozzle on the outlet end thereof;

electrical switch means mounted on said housing means for electrically connecting said battery means and said motor means together to permit energization of said motor means when said switch means is closed; and manually actuated means movably supported on said housing means and coacting with said switch means for permitting selected actuation of said switch means.

9. A device according to claim 8, wherein said conduit means includes an elongated conduit portion which projects outwardly a substantial distance beyond the other end of said tubular housing portion and has said discharge nozzle on the outer free end thereof.

10. A device according to claim 9, wherein a trumpet-shaped cover is removably mounted on the outlet end of said conduit portion in surrounding relationship to the discharge nozzle.

* * * * *

UNITED STATES PATENT AND TRADEMARK OFFICE

CERTIFICATE OF CORRECTION

PATENT NO. : 3 943 660

DATED : March 16, 1976

INVENTOR(S) : Hideo Hosaka

It is certified that error appears in the above-identified patent and that said Letters Patent are hereby corrected as shown below:

Column 5, line 19; change "power" to ---powder---.

Signed and Sealed this

*fifteenth* Day of *June 1976*

[SEAL]

*Attest:*

RUTH C. MASON
*Attesting Officer*

C. MARSHALL DANN
*Commissioner of Patents and Trademarks*